US010617340B2

(12) United States Patent
Fritz et al.

(10) Patent No.: US 10,617,340 B2
(45) Date of Patent: *Apr. 14, 2020

(54) SYSTEM FOR WITHDRAWING BLOOD

(71) Applicant: Roche Diabetes Care, Inc., Indianapolis, IN (US)

(72) Inventors: Michael Fritz, Buerstadt (DE); Klaus-Dieter Sacherer, Kirchheim (DE); Hans List, Hesseneck-Kailbach (DE); Thomas Weiss, Mannheim (DE); Frank Deck, Niederkirchen (DE); Claudio Immekus, Tutschfelden (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 282 days.

This patent is subject to a terminal disclaimer.

(21) Appl. No.: 15/804,352

(22) Filed: Nov. 6, 2017

(65) Prior Publication Data
US 2018/0055431 A1     Mar. 1, 2018

Related U.S. Application Data

(63) Continuation of application No. 14/159,979, filed on Jan. 21, 2014, now Pat. No. 9,839,387, which is a (Continued)

(30) Foreign Application Priority Data

Oct. 31, 2000    (DE) .................................. 100 53 974

(51) Int. Cl.
    *A61B 5/151*       (2006.01)
    *A61B 5/15*        (2006.01)

(52) U.S. Cl.
    CPC ........ *A61B 5/15186* (2013.01); *A61B 5/1519* (2013.01); *A61B 5/150022* (2013.01);
(Continued)

(58) Field of Classification Search
    CPC ........ A61B 5/150022; A61B 5/150183; A61B 5/150412; A61B 5/150519;
(Continued)

(56) References Cited

U.S. PATENT DOCUMENTS 2,714,890 A     8/1955   Vang
3,086,288 A     4/1963   Balamuth et al.
(Continued)

FOREIGN PATENT DOCUMENTS

DE       28 03 345 B1    6/1979
DE       198 30 604 A1   2/2000
(Continued)

OTHER PUBLICATIONS

DE 28 03 345 B1 English Language Translation.

*Primary Examiner* — Jocelin C Tanner
(74) *Attorney, Agent, or Firm* — Woodard, Emhardt, Henry, Reeves & Wagner, LLP

(57) ABSTRACT

The present invention includes a system for withdrawing body fluids. The system includes a drive unit having a plunger which is moved from a resting position into a lancing position in order to carry out a lancing process and a lancing unit containing a lancet with a needle. The plunger and lancet are coupled together by a form fit in order to carry out a lancing process. The invention additionally concerns a method for temporarily extending a needle from a device for withdrawing body fluid as well as a lancing unit that can be attached to the drive unit.

23 Claims, 10 Drawing Sheets

Related U.S. Application Data continuation of application No. 13/270,609, filed on Oct. 11, 2011, now Pat. No. 8,636,758, which is a continuation of application No. 10/415,577, filed as application No. PCT/EP01/12527 on Oct. 30, 2001, now Pat. No. 8,043,317.

(52) U.S. Cl.
CPC ...... *A61B 5/15113* (2013.01); *A61B 5/15117* (2013.01); *A61B 5/15153* (2013.01); *A61B 5/15163* (2013.01); *A61B 5/150183* (2013.01); *A61B 5/15194* (2013.01); *A61B 5/150412* (2013.01); *A61B 5/150519* (2013.01); *A61B 5/150549* (2013.01); *A61B 5/150572* (2013.01); *A61B 5/150618* (2013.01); *A61B 5/150717* (2013.01)

(58) Field of Classification Search
CPC ........ A61B 5/150549; A61B 5/150572; A61B 5/150618; A61B 5/150717; A61B 5/15113; A61B 5/15117; A61B 5/15153; A61B 5/15163; A61B 5/15186; A61B 5/1519; A61B 5/15194
See application file for complete search history.

(56) References Cited

U.S. PATENT DOCUMENTS

| | | |
|---|---|---|
| 3,208,452 A | 9/1965 | Stern |
| 3,673,475 A | 6/1972 | Britton, Jr. |
| 3,832,776 A | 9/1974 | Sawyer |
| 4,077,406 A | 3/1978 | Sandhage et al. |
| 4,154,228 A | 5/1979 | Feldstein et al. |
| 4,203,446 A | 5/1980 | Hofert et al. |
| 4,223,674 A | 9/1980 | Fluent et al. |
| 4,230,118 A | 10/1980 | Holman et al. |
| 4,356,826 A | 11/1982 | Kubota |
| 4,449,529 A | 5/1984 | Burns et al. |
| 4,462,405 A | 7/1984 | Erhlich |
| 4,518,384 A | 5/1985 | Tarello et al. |
| 4,535,773 A | 8/1985 | Yoon |
| 4,553,541 A | 11/1985 | Burns et al. |
| 4,627,445 A | 12/1986 | Garcia et al. |
| 4,637,403 A | 1/1987 | Garcia et al. |
| 4,653,513 A | 3/1987 | Dombrowski |
| 4,750,489 A | 6/1988 | Berkman et al. |
| 4,787,398 A | 11/1988 | Garcia et al. |
| 4,794,926 A | 1/1989 | Munsch et al. |
| 4,823,806 A | 4/1989 | Bajada |
| RE32,922 E | 5/1989 | Levin et al. |
| 4,924,879 A | 5/1990 | O'Brien |
| 4,983,178 A | 1/1991 | Schnell |
| 4,995,402 A | 2/1991 | Smith et al. |
| 5,029,583 A | 7/1991 | Meserol et al. |
| 5,035,704 A | 7/1991 | Lambert et al. |
| 5,047,044 A | 9/1991 | Smith et al. |
| 5,097,810 A | 3/1992 | Fishman et al. |
| 5,145,565 A | 9/1992 | Kater et al. |
| 5,152,775 A | 10/1992 | Ruppert |
| 5,188,118 A | 2/1993 | Terwilliger |
| 5,189,751 A | 3/1993 | Giuliani et al. |
| 5,196,025 A | 3/1993 | Ranalletta |
| 5,222,504 A | 6/1993 | Solomon |
| 5,230,428 A | 7/1993 | McShane |
| 5,279,294 A | 1/1994 | Anderson et al. |
| 5,290,254 A | 3/1994 | Vaillancourt |
| 5,318,584 A | 6/1994 | Lange et al. |
| 5,320,808 A | 6/1994 | Holen et al. |
| 5,366,469 A | 11/1994 | Steg et al. |
| 5,368,047 A | 11/1994 | Suzuki et al. |
| 5,415,169 A | 5/1995 | Siczek et al. |
| 5,423,847 A | 6/1995 | Strong et al. |
| 5,472,427 A | 12/1995 | Rammler |
| 5,474,084 A | 12/1995 | Cunniff |
| 5,514,152 A | 5/1996 | Smith |
| 5,529,074 A | 6/1996 | Greenfield |
| 5,549,568 A | 8/1996 | Shields |
| 5,554,166 A | 9/1996 | Lange et al. |
| 5,575,403 A | 11/1996 | Charlton et al. |
| 5,578,014 A | 11/1996 | Erez et al. |
| 5,630,986 A | 5/1997 | Charlton et al. |
| 5,632,410 A | 5/1997 | Moulton et al. |
| 5,695,472 A | 12/1997 | Wyrick |
| 5,700,695 A | 12/1997 | Yassinzadeh et al. |
| 5,714,390 A | 2/1998 | Hallowitz et al. |
| 5,720,924 A | 2/1998 | Eikmeier et al. |
| 5,738,244 A | 4/1998 | Charlton et al. |
| 5,758,643 A | 6/1998 | Wong et al. |
| 5,776,157 A | 7/1998 | Thorne et al. |
| 5,788,651 A | 8/1998 | Weilandt |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,863,800 A | 1/1999 | Eikmeier et al. |
| 5,871,494 A | 2/1999 | Simons et al. |
| 5,871,495 A | 2/1999 | Mueller |
| 5,879,311 A | 3/1999 | Duchon et al. |
| 5,880,829 A | 3/1999 | Kauhaniemi et al. |
| 5,885,211 A | 3/1999 | Eppstein et al. |
| 5,891,053 A | 4/1999 | Sesekura |
| 5,916,229 A | 6/1999 | Evans |
| 5,935,075 A | 8/1999 | Casscells et al. |
| 5,938,679 A | 8/1999 | Freeman et al. |
| 5,951,582 A | 9/1999 | Thorne et al. |
| 5,968,063 A | 10/1999 | Chu et al. |
| 5,971,941 A | 10/1999 | Simons et al. |
| 5,997,561 A | 12/1999 | Bocker et al. |
| 6,022,324 A | 2/2000 | Skinner |
| 6,027,459 A | 2/2000 | Shain et al. |
| 6,036,924 A | 3/2000 | Simons et al. |
| 6,048,352 A | 4/2000 | Douglas et al. |
| 6,071,294 A | 6/2000 | Simons et al. |
| 6,090,078 A | 7/2000 | Erskine |
| 6,093,156 A | 7/2000 | Cunningham et al. |
| 6,110,160 A | 8/2000 | Faerber |
| 6,117,630 A | 9/2000 | Reber et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,190,398 B1 | 2/2001 | Schraga |
| 6,193,673 B1 | 2/2001 | Viola et al. |
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,258,112 B1 | 7/2001 | Schraga |
| 6,261,241 B1 | 7/2001 | Burbank et al. |
| 6,261,245 B1 | 7/2001 | Kawai et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |

(56) References Cited

U.S. PATENT DOCUMENTS

| | | |
|---|---|---|
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,540,762 B1 | 4/2003 | Bertling |
| 6,783,537 B1 | 8/2004 | Kuhr et al. |
| 8,636,758 B2 | 1/2014 | Fritz et al. |
| 9,839,387 B2 * | 12/2017 | Fritz .............. A61B 5/15186 |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0082543 A1 | 6/2002 | Park et al. |
| 2002/0103499 A1 | 8/2002 | Perez et al. |
| 2003/0083685 A1 | 5/2003 | Freeman et al. |
| 2003/0083686 A1 | 5/2003 | Freeman et al. |
| 2003/0088191 A1 | 5/2003 | Freeman et al. |
| 2003/0153939 A1 | 8/2003 | Fritz et al. |
| 2003/0199893 A1 | 10/2003 | Boecker et al. |
| 2003/0199896 A1 | 10/2003 | Boecker et al. |
| 2003/0199897 A1 | 10/2003 | Boecker et al. |
| 2003/0199900 A1 | 10/2003 | Boecker et al. |
| 2003/0199901 A1 | 10/2003 | Boecker et al. |
| 2003/0199902 A1 | 10/2003 | Boecker et al. |
| 2003/0199903 A1 | 10/2003 | Boecker et al. |
| 2003/0199904 A1 | 10/2003 | Boecker et al. |
| 2003/0199906 A1 | 10/2003 | Boecker et al. |
| 2003/0199907 A1 | 10/2003 | Boecker et al. |
| 2003/0199908 A1 | 10/2003 | Boecker et al. |
| 2003/0199909 A1 | 10/2003 | Boecker et al. |
| 2003/0199910 A1 | 10/2003 | Boecker et al. |
| 2003/0199911 A1 | 10/2003 | Boecker et al. |
| 2003/0233112 A1 | 12/2003 | Alden et al. |
| 2003/0233113 A1 | 12/2003 | Alden et al. |

FOREIGN PATENT DOCUMENTS

| | | |
|---|---|---|
| EP | 0 565 970 B1 | 6/1994 |
| JP | H04-194660 A | 7/1992 |
| JP | H09-276235 | 10/1997 |
| JP | 2000-116768 A2 | 4/2000 |
| PL | 171458 B1 | 11/1993 |
| PL | 185564 B1 | 11/1997 |
| PL | 189108 B1 | 6/2005 |
| WO | WO 1993/02720 A1 | 2/1993 |
| WO | WO 1993/12726 A1 | 7/1993 |
| WO | WO 1997/42888 A1 | 11/1997 |
| WO | WO 2001/00090 A1 | 1/2001 |
| WO | WO 2001/34029 A1 | 5/2001 |
| WO | WO 2001/66010 A1 | 9/2001 |
| WO | WO 2002/056769 A1 | 7/2002 |
| WO | WO 2003/088834 A1 | 10/2003 |
| WO | WO 2003/088835 A2 | 10/2003 |

\* cited by examiner

SYSTEM FOR WITHDRAWING BLOOD

CROSS REFERENCE TO RELATED APPLICATIONS

This application is a continuation of U.S. patent application Ser. No. 14/159,979 filed Jan. 21, 2014, which is a continuation of U.S. patent application Ser. No. 13/270,609 filed Oct. 11, 2011, now U.S. Pat. No. 8,636,758, which is a continuation of U.S. patent application Ser. No. 10/415,577 filed Apr. 30, 2003, now U.S. Pat. No. 8,043,317, which is the National Stage of International Patent Application No. PCT/EP2001/12527 filed Oct. 30, 2001, which claims the benefit of German Patent Application No. 100 53 974.2, filed Oct. 31, 2000, the entire disclosures of which are hereby incorporated by reference.

FIELD OF INVENTION

The present invention includes a system for withdrawing body fluids from a part of the body for example, the finger pad, by producing a small puncture wound.

BACKGROUND AND SUMMARY

In the field of clinical diagnostics it is necessary to obtain samples of body fluids, in particular blood samples, in order to detect constituents thereof. If a larger amount of blood is required, it is usually collected with a syringe or similar device by piercing a particular blood vessel. However, the field of the present invention is one in which only small amounts of sample in the range of a few microliters (μl) or less are necessary to determine analytical parameters. Such a procedure is especially widespread for measuring the blood sugar level, coagulation parameters, triglycerides, HBA1c, or lactate.

In the field of diabetes it has now become accepted practice for diabetics to monitor their blood sugar level (so-called home-monitoring). This is necessary to maintain a blood sugar level which is within the normal range by administering calculated doses of insulin. If a diabetic becomes hypoglycaemic he may become unconscious possibly resulting in the death of the patient. If, on the other hand, a patient has a blood sugar level which is too high, this can lead to serious secondary effects such as loss of sight and gangrene. Small and easy-to-handle blood withdrawal devices, so-called lancing aids that can be simply and reliably operated by the user or hospital and nursing staff are now commonly used to withdraw the blood required to measure the blood sugar level. Recently systems for withdrawing interstitial fluid have also been disclosed which can in principle be used to carry out such analyses.

An emerging problem in this field is contamination and injury by used lancets. In many commercial devices the lancet is removed or ejected after the lancing process. The needle of the lancet which is exposed in such cases can lead to injuries that may result in infections. Consequently in some countries attempts are already being made to prohibit blood withdrawal systems in which the needle tip is freely accessible after use.

Various variants of blood withdrawal systems have been described in prior art documents in which the needle is protected after the lancing process. A cap in which a lancet is located is described in U.S. Pat. No. 5,314,442. In order to carry out a lancing process, the lancet is pushed within the cap by a plunger or a similar device in such a manner that the needle exits through an opening. After the piercing the lancet is retracted inside the cap and flexible elements on the lancet ensure that the lancet needle can no longer emerge without the action of the plunger. Systems based on a similar principle are described in U.S. Pat. Nos. 4,990,154 and 5,074,872 and PCT Application WO 00/02482. Another system in which a lancet is retracted into a cap by an incorporated spring is described in German Patent No. DE 198 55 465. Although the said documents already solve the problem of contamination or injury to the user, within the prior art the drive mechanism is only coupled to the lancet by a press fit. The puncture depth of the needle is limited by a stop. However, it has turned out that the lancet impacting on the stop vibrates the needle which increases the pain caused by the puncturing. This problem is described in more detail in European Patent No. EP 0 565 970.

An object of the present invention was to suggest a system for withdrawing body fluid which, on the one hand, avoids contamination or infection by used lancets and, on the other hand, allows a substantially pain-reduced lancing for the user. Another object was to simplify the systems of the prior art and make them more cost-effective and, in particular, to propose a design which can be miniaturized. The latter is especially important in order to provide a system that operates with lancets in magazines and allows a user to change a lancet that has not yet been used without having to carry out complicated handling steps.

The said objects of the present invention are achieved by embodiments of systems for withdrawing body fluid which have a drive unit with a plunger which is moved from a resting position into a lancing position in order to carry out a lancing process. The systems also comprise a lancing unit in which a lancet with a needle is located adjacent to the plunger in its resting position, and is arranged within the lancing unit so that the needle is displaced by the plunger when it moves into the lancing position in such a manner that the needle at least partially emerges from the lancing unit through an outlet opening. An important feature of the system is that the plunger and lancet are interconnected by a form fit in order to carry out the piercing process.

A characteristic feature of a form fit in the sense of this invention is that it enables the lancet and driving plunger to be coupled with little expenditure of force. There are two basic ways for achieving a form fit. In a first variant the lancet and driving plunger are coupled by close fitting in such a manner that a holding element is enclosed. The form which closes is referred to as a holding device within the scope of the invention. If the holding device is located on the lancet, the driving plunger has a holding element, but if the holding device is on the driving plunger, the holding element is located on the lancet. FIGS. 1 and 2 show practical embodiments. This variant of the form fit is preferably achieved in that a longitudinal movement in the piercing direction causes a transverse movement of the holding elements of a (initially opened) holding device which thereby close around a holding area.

The holding element is preferably (at least partially) gripped from behind when the holding device closes in such a manner that the lancet is carried when the driving plunger is pulled back—at least to a possible opening of the holding device. Furthermore, it is preferred that the geometry of the holding device and holding area match in such a manner that there is no movement or only a slight movement in the direction of the lancing movement after the form fit and that the movement of the driving plunger in the lancing direction as well as in the opposite direction is converted without any play in the movement of the lancet. This can be achieved when the longitudinal extension of the chamber in the closed holding device is identical to or only negligibly larger than the longitudinal extension of the holding area (see FIG. 1). In another embodiment of this variant the longitudinal extension of a recess in the holding area and holding elements on the holding device correspond in such a manner that transport in the lancing direction is possible without essentially any play (see FIG. 2).

In a second variant of the form fit, the holding device and the holding area are essentially dimensionally stable and the holding area is enclosed by the holding device. The profiles of these two units move into each other. Since the units are dimensionally stable, a complete enclosure is not possible and the profiles must be open to such an extent that they can be moved into each other. This joining movement (of at least one path component) is at right angles to the lancing direction resulting in a connection which is also essentially without any play in the lancing direction (see FIG. 4). Finally, coupling can also be achieved by a movement having components at right angles as well as parallel to the lancing direction (see FIG. 7).

The system according to the invention for withdrawing blood has a drive unit with a plunger which moves a lancet from a resting position into a lancing position. A number of drive mechanisms are known from the prior art that can be used in the field of blood withdrawal devices. In particular, drive mechanisms are used on a large scale which obtain their energy from a previously tensioned spring. Drive units are preferably used within the scope of the present invention which enable a guided movement of the plunger and the lancet as a result of the form-fitting connection. A guided movement means that the lancet pierces the body over a predetermined path and is also removed from the body over a predetermined path-time course. In conventional systems of the prior art based on a combination of a spring and a stop the path-time course is influenced by numerous parameters such as manufacturing tolerances (frictional conditions in the system, strength of the spring, etc.) as well as the skin surface. It has turned out that a guided movement of the lancet, for example, by means of a guide block as described in European Patent No. EP 565 970, is advantageous with regard to the pain caused by the piercing. With regard to the drive unit, reference is herewith made to the preferred drive mechanisms of European Patent No. EP 565 970 and its U.S. counterpart, U.S. Pat. No. 5,318,584, the disclosures of both of which are herein expressly incorporated by reference, and U.S. Pat. No. 4,924,879.

An important aspect of the invention is a lancing unit containing at least one lancet that can be removed from the drive unit. The lancing unit comprises a housing in which the lancet is arranged in a resting position. This prevents the lancet from causing injury or being contaminated before or after use. The housing can be designed such that a single lancet is located therein or the housing can have the form of a magazine containing a plurality of lancets. Usually the lancets in a magazine are located in separate chambers to prevent contamination of unused lancets by ones that have already been used. The housing of the lancing unit is designed such that it can be attached to the drive unit. For this purpose the lancing unit can, for example, have the shape of a cap which is mounted on the drive unit. Such embodiments are described, for example, in U.S. Pat. Nos. 5,314,442, 4,990,154 and 5,074,872, the disclosures of all which are herein expressly incorporated by reference.

Embodiments are also possible in which the lancing unit is permanently connected to the drive unit or is an integral component of the drive unit. This can be used for systems with a magazine such that the entire unit can be discarded after the magazine has been used. In the case of a lancing unit in the form of a magazine, it can, for example, have chambers arranged next to one another in which the lancets are located and the chambers are positioned successively relative to the drive unit such that the lancets can be coupled to the plunger of the drive unit. A magazine in the form of a barrel having chambers arranged parallel to the longitudinal axis of the barrel in which the lancets are located is another possible embodiment. In a similar manner to a revolver barrel, such a magazine can be repeatedly attached to the drive unit.

Another requirement for the lancing unit is that the sterility of the lancets must be ensured over a long time period. The lancing unit can be sterilized by gamma irradiation, which is commonly used in the prior art. In order to maintain the sterile conditions, the lancing unit can be sealed in an enclosing package, for example, a polyethylene bag. In another embodiment, the openings of the lancing unit (for inserting the plunger and for the exit of the needle tip) can be closed by sealing foils. These can, for example, be detachable sealing foils that are removed by the user before use. However, thin foils can also be used which are pierced before use by the plunger or by the needle tip so that the user does not have to carry out additional handling steps. Such foils can be manufactured as a part of the manufacturing process for the lancing unit, which is usually an injection moulding process.

In another embodiment, the needle tip is protected from contamination by an elastomer, which is removed before the lancing or is pierced during the lancing process in order to expose the needle tip. Such a protection of the needle from contamination is described in the PCT Published Application No. WO 01/66010, the disclosure of which is herein expressly incorporated by reference.

One or more lancets with a needle are located within the lancing unit. Apart from devices that may be present on the lancet that enable a form-fitting connection to a plunger, lancets can be used within the scope of this invention that are well-known in the prior art. Such a lancet usually has a main body made of plastic in which a metal needle is located. However, lancets without a separate main body are also possible (such as metal needles having a thickening at the rear end used as a holding area).

An important aspect of the invention is that the plunger of the drive unit and the lancet for carrying out the lancing process are connected together by a form fit. In this respect the invention differs substantially from the prior art where the lancet and drive are mechanically coupled by means of a press fit (for example, U.S. Pat. Nos. 5,314,442, 4,990,154, and 5,074,872), a locking device (PCT Published Application No. WO 00/02482), by clamping (U.S. Pat. No. 3,030,959) or by simple pressure (German Patent No. DE 198 55465). A form fit is characterized in that a mechanically reliable coupling occurs between the drive and the lancet without having to apply a substantial pressure on the lancet in the direction of the lancing movement.

In the devices of the prior art which work with a press fit, a spring element (e.g. German Patent No. DE 198 55 465) or a retaining element (e.g. PCT Published Application No. WO 00/02482) have to be provided in the cap which contains the lancet. This element is designed such that the lancet does not emerge from the cap when the lancing unit is coupled to the drive unit.

However, spring elements in the lancing unit increase the manufacturing costs which is particularly serious since the lancing unit is a consumable. Furthermore, the drive unit requires an additional force to overcome a retaining element which also leads to vibrations of the needle which have an adverse effect on the puncturing pain. In addition, a guided movement which comprises a retraction of the lancet is problematic in systems which utilize a press fit since this can detach the press fit. Although the locking device described in PCT Published Application No. WO 00/02482 is directed to this problem, it is difficult to accomplish technically. In particular, it is difficult to establish such a locking device in a continuous manufacturing process since even slight variations in the material or the process conditions can result in a loss of the function of the device.

Another characteristic of the device described in PCT Published Application No. WO 00/02482 is that the locking occurs in a path range which serves to puncture the body. The fluctuations in force occurring during the locking and the vibrations have a disadvantageous effect on the pain of incision. Another characteristic of the device is that the needle remains in the body after the incision and is not actively retracted. The needle is only retracted when the cap is removed from the drive mechanism. In contrast, a form fit between the driving plunger and lancet according to the present invention enables the plunger and lancet to be connected without having to apply a particular force in the direction of the puncture. The form-fitting connection can be utilized to actively retract the needle after the incision. This ability to actively control the path-time curve of the needle by means of the drive unit enables the lancing to be carried out with very little pain.

Another property of the form fit according to the invention becomes apparent by examining U.S. Pat. No. 3,030,959. In an apparatus according to this U.S. Pat. No. 3,030,959, needles which are arranged in a tube are held successively by a clamping device which is similar to a propelling pencil. In addition to the contamination problems caused by used needles, which are not solved by this apparatus, the positioning of the needles in the axial direction (i.e. in the lancing direction) is not defined. In the same way as the length of the protruding pencil tip can be freely selected by the user in the case of a propelling pencil, the axial positioning of the needle depends on the adjustment by the user. In contrast, in the present invention the lancet and drive unit have matching holding areas and holding devices to create a form fit. The geometric design of the holding area and holding device enables the axial positioning of the lancet to be defined and thus enables an exact control of the puncture depth. Thus the use of a form fit avoids a force peak in the axial direction when the lancet and driving plunger are coupled together and also enables an exact axial positioning. In the case of a form fit, a form (holding device) encloses another form (holding area). In this sense "enclosing" means a movement of parts of the device at right angles to the lancing direction and alternatively a form fitting interlocking of two shaped bodies whose shape does not change.

In a preferred embodiment, the holding device is open and closes around the holding area when it is inserted into the holding device. This enclosing can occur, in particular, as a result of a longitudinal movement which is converted into a transverse movement of the holding elements of the holding device which are at right angles to the longitudinal direction of movement. One method of achieving this conversion of a longitudinal movement into a transverse movement is to insert or slide the holding device by means of the longitudinal movement into a tapered channel (e.g. into a sleeve) (see FIG. 1). In this connection, tapered not only refers to continuously tapering channels, but also to channels whose inner width decreases in the longitudinal direction. In this connection a channel does not have to be a body with a closed circumferential surface. If, for example, the holding device has two opposing hooks as shown in FIG. 1, it only requires two walls whose distance to one another decreases.

Another possibility is to close the holding device by releasing a tensioned spring (see FIG. 2) which can, for example, be achieved by moving the holding device in a broadening channel.

DETAILED DESCRIPTION OF DRAWINGS

Figure 1:
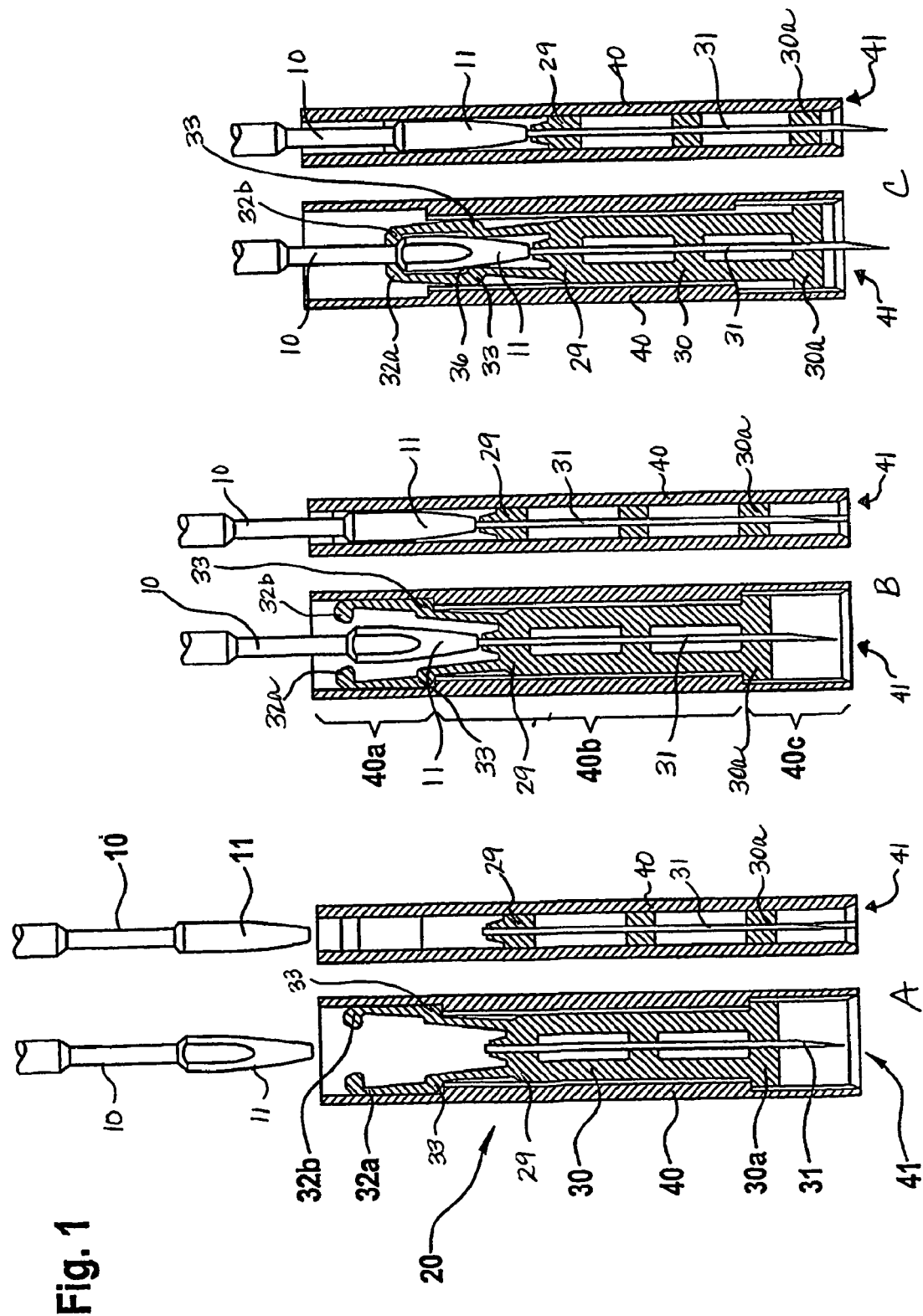
FIGS. 1A-1C are cross-sectional views through a lancing unit having a holding device on the lancet, shown at three different positions (A,B,C).

FIGS. 1A-1C show a blood withdrawal system according to a first embodiment of the invention. FIGS. 1A-1C only show partial aspects of the system. The figures do not show the drive unit for the plunger 10 nor the housing of the drive unit to which the lancing unit 20 is attached. The driving device described in European Patent No. EP 0 565 970 and its U.S. counterpart, U.S. Pat. No. 5,318,584, is suitable as a drive unit for the plunger 10.

The six views shown in FIGS. 1A-1C show how the form-fitting coupling between the driving plunger 10 and the lancet 30 occurs during the actual lancing process. Two cross-sectional views along the longitudinal axis of the system in perpendicular planes are shown for each of the three FIGS. 1A, 1B, and 1C. The left view in FIG. 1A shows that the lancet 30 is arranged within a sleeve 40. The lancet 30 has a main body manufactured from plastic and a needle 31 made of steel that is injection moulded therein in the preferred embodiment, although any suitable method of mounting the needle 31 into the lancet 30 may be used. The end of the lancet 30 facing away from the needle tip has a holding device 29 comprising holding elements in the form of two hooks 32a, 32b. When the plunger 10 of the driving unit is inserted into the lancet 30, a thickened region at the front end of the plunger which serves as a holding area 11 passes between the hooks 32a, 32b and finally strikes the rear end of the needle 31, as shown in FIG. 1B. It is also possible to allow the plunger 10 to strike the main body of the lancet 30 instead of the rear end of the needle 31. However, a direct contact with the needle 31 is advantageous since the length of the needle 31 can be very exactly controlled in the manufacturing process and hence an accurate control of the puncture depth is possible.

As shown in FIG. 1C, as the plunger 10 penetrates the lancet 30 further it pushes the lancet 30 within the sleeve 40 towards the exit opening 41 such that finally the tip of the needle 31 protrudes beyond the exit opening 41 and pierces a tissue lying underneath. The transition shown in FIGS. 1B and 1C, shows that the hooks 32a, 32b on the lancet 30 close around the holding area 11 of the plunger 10 as soon as the lancet 30 is displaced within the sleeve 40. The hooks 32a, 32b on the lancet 30 grip around the holding area 11 of the plunger 10 in such a manner that a form-fitting connection is formed which not only enables a forward movement of the lancet 30 in order to carry out an incision, but also an active retraction of the lancet 30 controlled by the drive unit which is essentially without play. This is possible because the end of the holding area 11 rests on the end of the needle 31 and by the hooks 32a, 32b which grip behind the rear end of the holding area 11. The length of the holding area 11 and the longitudinal extension of the chamber 36 in the closed holding device are designed to match one another in such a manner that the lancet 30 can be driven in the lancing direction without play.

The arrangement of the lancet 30 or the holding device 29 in a tapered sleeve 40 enables a longitudinal movement of the lancet in the lancing direction to be converted into a transverse movement of the elements of the holding device 29 which enables a form fit with the holding area 11 of the drive. The figures show that the sleeve 40 has a middle region 40b which is tapered compared to the upper region 40a. As a result of this tapering the hooks 32a, 32b of the lancet 30 are pressed together when the lancet 30 is moved in the sleeve 40 in the direction of the longitudinal axis such that the holding area 11 is enclosed. The lancing unit 20 has been designed such that the lancet 30 is held within the sleeve 40 when it is not acted upon by the plunger 10. This ensures that the needle 31 is located within the sleeve 40 when it is not actuated and thus there is no injury or contamination caused by a protruding needle tip.

The lancet 30 is effectively prevented from sliding through the sleeve 40 towards the exit opening 41 by the fact that the hooks 32a, 32b have a shoulder 33 which rests on an edge of the middle region 40b. The slope of these edges and the flexibility of the hooks 32a, 32b can be matched in such a manner that an insertion into the tapered region can occur with a small force, but on the other hand, an unintentional sliding through is efficiently prevented. In order to prevent the lancet 30 from sliding out of the sleeve 40 in the opposite direction to the lancing direction, the embodiment shown provides a widened part 40c at the lower end of the sleeve 40 and a corresponding widened part 30a at the lower end of the main lancet body.

As shown in FIG. 1C the needle tip is still within the sleeve 40 when the holding area 11 strikes the end of the needle 30. Lancing unit 20 is designed this way so that the shock caused by the impact has no influence on the lancing process in the tissue which thus avoids incision pain caused by such a vibration.

According to the present invention it is preferred that the system is designed such that after lancet 30 has been extended to the lancing position shown in FIG. 1C, the plunger 10 is retracted in the reverse direction such that the plunger 10 is disconnected from the lancet 30 and the lancet 30 is again located completely within the sleeve 40. There are two main variants for coupling the plunger 10 to the lancet 30. In a first variant, the housing (not shown), drive unit (not shown) and lancing unit 20 are matched in such a manner that the plunger 10 in the initial state is located completely outside the lancing unit 20, as shown in FIG. 1. The plunger 10 has to travel through a relatively long path in order to carry out the piercing process. However, the plunger 10 is located completely outside the sleeve 40 such that a transverse movement is possible. Accordingly, the first variant can be used for systems having a lancet magazine in which various sleeves are successively moved under the plunger. In a second variant, the coupling of the lancing unit to the drive unit already results in a positioning according to FIG. 1B, or even towards the lancing position, shown in FIG. 1C. In such an embodiment the path which the plunger has to travel through can be kept very small.

Figure 2:
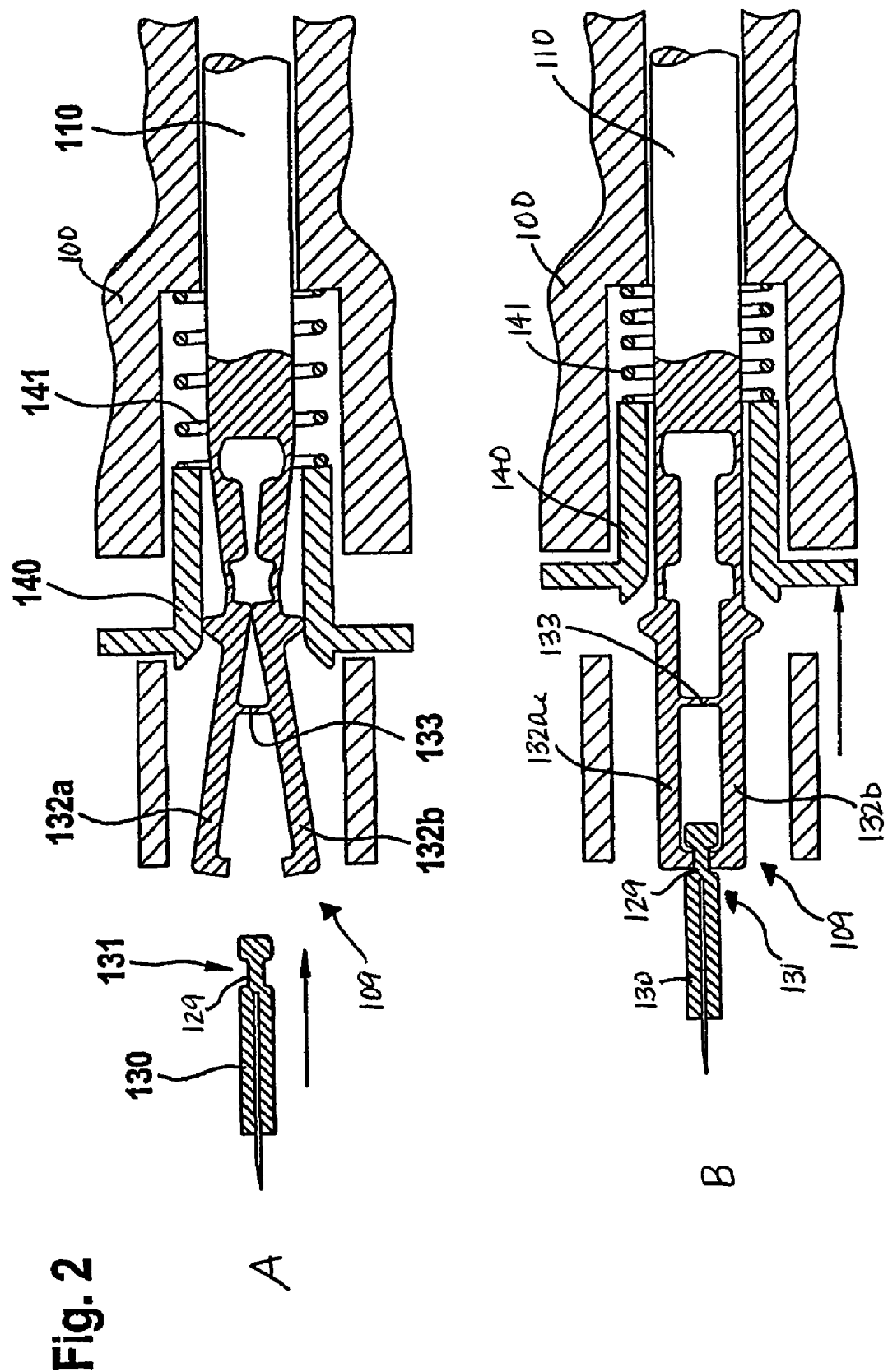
FIGS. 2A and 2B are cross-sectional views through a section of the system having a holding device on the drive unit, shown at two different positions (A,B).

Referring now to FIGS. 2A and 2B, a second embodiment of the invention in which the lancet 130 has a holding area 131 and the drive unit 100 has a holding device 109 is shown. FIGS. 2A and 2B also show the area of the system which is used to hold the lancet 130 but does not show the drive unit. In connection with this embodiment it is also advantageous to use a drive unit which moves the plunger 110 in a guided manner. The front end of the plunger 110 carries a holding device 109 comprising holding elements in the form of two hooks 132a, 132b which are connected together by a flexible bridge 133. The arrangement forms a spring element. In FIG. 2A, these hooks 132a, 132b are spread since their rear ends are held together by a sleeve 140. When the lancet 130 is inserted the sleeve 140 is simultaneously pushed against a spring 141 which releases the rear ends of the hooks 132a, 132b and the front ends of the hooks 132a, 132b close around the holding area 131 of the lancet 130 in a form-fitting manner. The holding area 131 of the lancet 130 has a recess 129 into which the hooks 132a, 132b of the holding device 109 engage. The longitudinal extension (in the lancing direction) of the engaging ends of the holding device 109 and the longitudinal extension of the recesses are essentially identical so that this arrangement can be used to carry out a guided, essentially play-free lancing movement. Also in this embodiment, a longitudinal movement of the holding device 109 is converted into a transverse movement of the hooks 132a, 132b.

Figure 3:
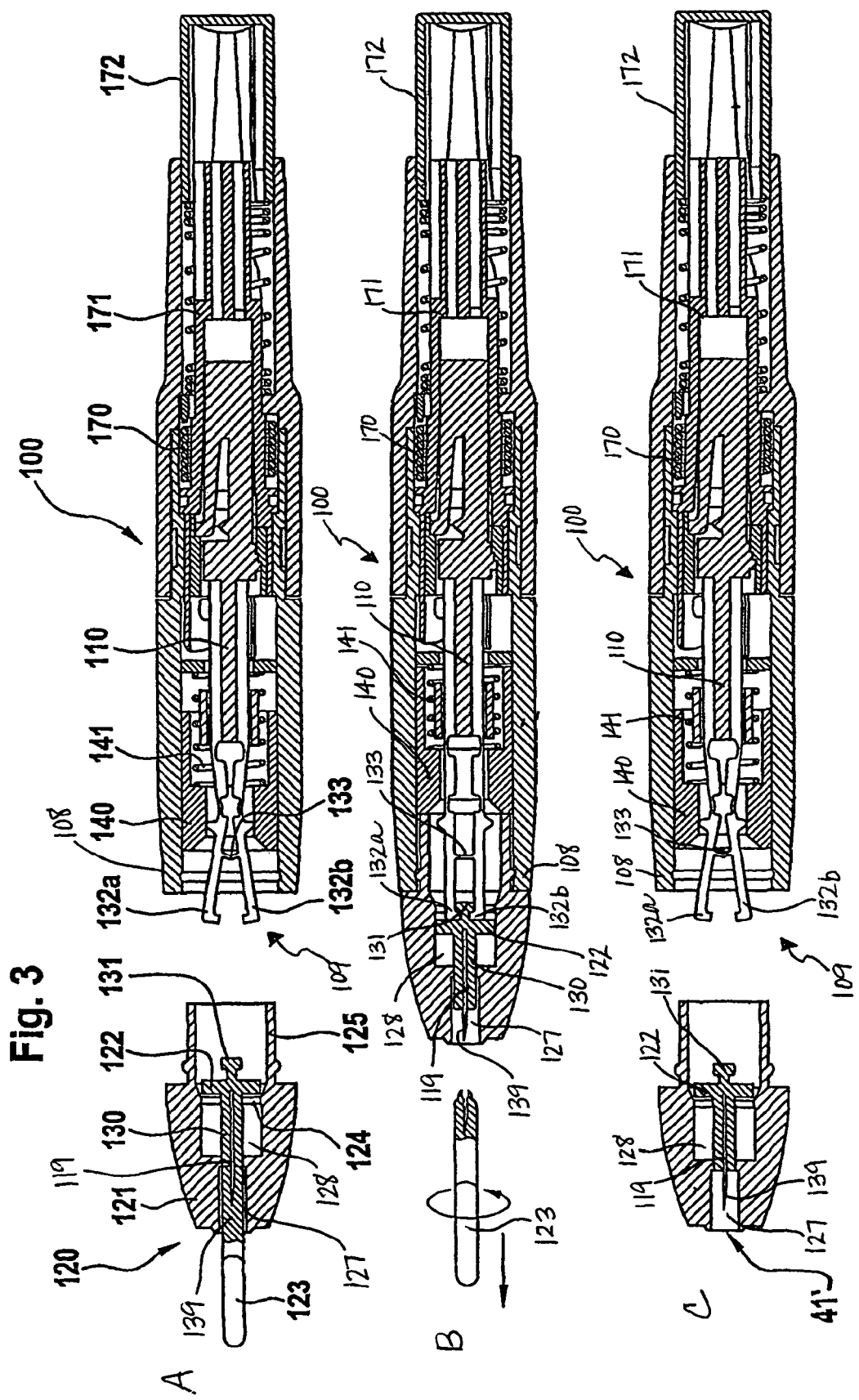
FIGS. 3A-3C are cross-sectional views through the total system, shown at three different positions (A,B,C).

Referring now to FIGS. 3A-3C, a system according to the present invention based on the form-fitting coupling principle of FIGS. 2A and 2B is shown. The drive unit 100 is based on the Softclix® instrument which is described in European Patent No. EP B 0 565 970 and its U.S. counterpart, U.S. Pat. No. 5,318,584. European Patent No. EP B 0 565 970 shows, in particular, how the rotary movement of the sleeve 171 mediated by the drive spring 170 is converted into a translational movement of the plunger 110. The tensioning of the drive spring 170 by depressing the pressure button 172 and a suitable mechanical transmission therefor are described in the European Patent Application No. EP 0 010 2503.0, the disclosure of which is herein expressly incorporated by reference. The front end 108 of the drive unit 100 has a holding device 109 comprising two holding elements, in this specific case hooks 132a, 132b.

As already explained for FIGS. 2A and 2B, the hooks 132a, 132b are connected together in a middle region via a flexible bridge 133 or a joint. On the side of the hook facing away from the bridge 133, the holding device 109 is held by a sleeve 140 in such a manner that the hooks 132a, 132b are opened as shown in FIGS. 3A and 3C. The sleeve 140 is kept in position by means of a spring 141 located in the driving unit 100. FIG. 3A also shows a lancing unit 120 where a lancet 130 is arranged in a cap 121. The rear end of the lancet 130 has a holding area 131 which is gripped by hooks 132a, 132b of holding device 109. The outer body of the lancet has a narrow region 119 at the front and a flange 122 situated between the narrow region 119 and the holding area 131. The tip of the lancet 139 is protected from contamination and mechanical influences by a twist-off plastic body 123. The inside of the cap 121 has a passage 127 for the narrow region 119 of the lancet and a widened channel 128 with an enlarged cross-section which is suitable for receiving the flange 122. A bead 124 is located within this widened channel 128 of the cap 121 which prevents the flange 122 from sliding through into the widened channel 128. The cap 121 also has a sleeve 125 which serves to slide back the sleeve 140 of the drive unit 100 when the lancing unit 120 is placed on the drive unit 100. This process is illustrated by both FIGS. 3A and 3B.

When the sleeve 140 is pushed rearward by the sleeve 125, the holding device 109 is released such that it can surround the holding area 131 of the lancet 130 as shown in FIG. 3B. The system is now prepared for use by pressing the button 172 and twisting off the protective part 123 of the lancet 130. A lancing process is then carried out with the device shown in FIG. 3B by placing the front end of the cap 120 on a part of a tissue and the drive unit 100 is activated by actuating a trigger mechanism. After the lancing process is completed the cap 121 is pulled from the drive unit 100 in the direction of the longitudinal axis which retracts the flange 122 behind the bead 124 so that the contaminated lancet tip 139 can no longer emerge from the cap 121. In the stage shown in FIG. 3C, the lancing unit 120 can be discarded or be used for further sampling processes after coupling to the drive unit 100.

Figure 4:
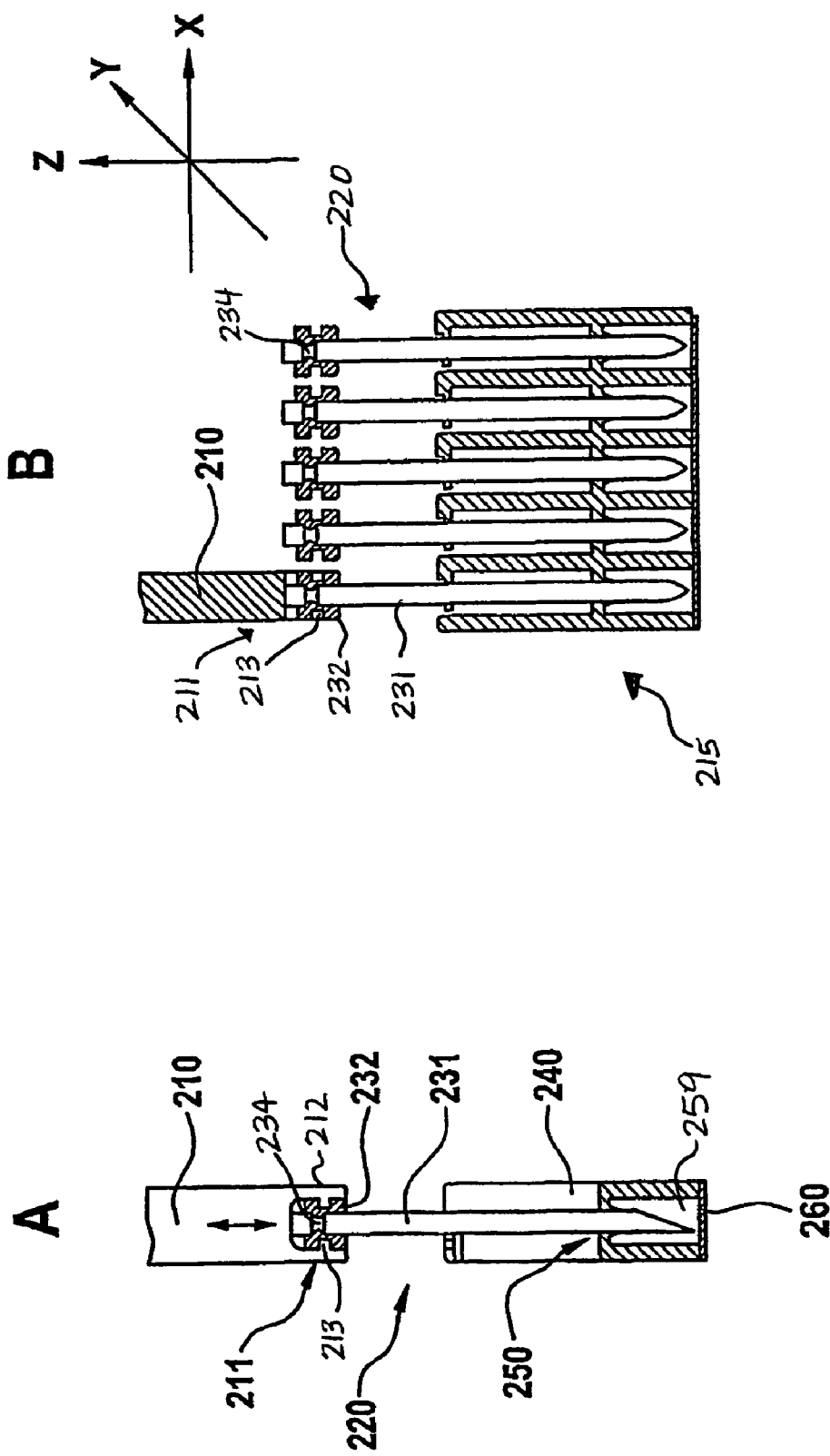
FIG. 4A is a side view of a section of the system with a dimensionally stable holding device on the drive unit.
FIG. 4B is a side view of a magazine of lancing units.

FIGS. 4A and 4B show another embodiment of the invention in which the form fit between the lancet unit 220 and the drive (not shown) is achieved by a form-fitting connection of geometrically matching holding areas 232 and holding devices 211. FIG. 4A shows a lancing unit 220 which has a sleeve 240 in which a metal needle 231 is located. The sleeve 240 has a thin cross wall 250 which holds the metal needle 231 relative to the sleeve 240. This cross wall 250 is preferably moulded at the same time as the needle 231 is moulded into the plastic. Due to the relatively small thickness of the cross wall 250, the mechanical connection between the sleeve 240 and needle 231 can be released during the lancing process such that the needle 231 slides past the wall 250. The exit opening 259 of the sleeve 240 is closed with a thin foil 260 which is pierced during the lancing process. The upper end of the needle 231 carries an injection moulded holding area 232. For mechanical stabilization the needle 231 has a taper around which the holding area 232 is injection moulded to prevent axial slipping. The needle 231 can also be held in the sleeve 240 by roughening the outer surface of the needle 231, or by means of a thickening or bend in the needle 231 in the area of the sleeve 240. The driving plunger 210 of this embodiment has a holding device 211 at its lower end 212 which embraces the holding area 232 in a form-fitting manner as shown. The side of the holding device 211 is open such that the plunger 210 is displaced parallel to the needle 231. The holding device 211 can be moved to the level of the holding area 232 and can be engaged with the holding area 232 of the needle 231 by moving it at right angles to the axis of the needle 231 or to the direction of lancing. After the form fit is achieved in this manner, the needle 231 can be propelled by the plunger 210 in the direction of lancing and can also be actively retracted. In the example shown, the holding area 232 of the needle 231 has a recess 234 into which a projecting part 213 of the holding device 211 engages during the coupling such that the two members are connected together without essentially any play in the direction of lancing.

A magazine 215 is shown in FIG. 4B which is composed of lancing units 220 according to FIG. 4A. With reference to the coordinate system shown, the driving plunger 210 can engage with the holding area 232 of the needle 231 or the form fit can be released again by movement in the Y direction (perpendicular to the plane of the drawing). When the form fit is released the driving plunger 210 can be moved in the X direction (right/left) to the level of another lancet unit 220 and in turn engage with this lancet unit 220 by movement in the Y direction such that the lancet unit 220 of a magazine 215 can be successively processed. After the form fit the needles 231 can be actively moved in a positive as well as a negative Z direction (upwards/downwards).

As an alternative to the coupling according to FIG. 4B which requires a movement of the driving plunger 210 in the X and in the Y direction, a coupling movement can also be accomplished by a movement in the X direction only. For this purpose the driving plunger 210, for example, has two opposing hooks between which a passage for the holding area of the lancet is provided. By movement in the X direction the plunger 210 can now be moved from lancet to lancet in order to carry out a lancing process in the Z direction. If the driving plunger 210 is at the level of a lancet in the X direction, the holding device of the plunger encloses the holding area of the lancet in a form-fitting manner and the lancet can be moved by the plunger in the Z direction in a guided manner. As a result the plunger carries out a lancing movement and also actively retracts the lancet.

Figure 5:
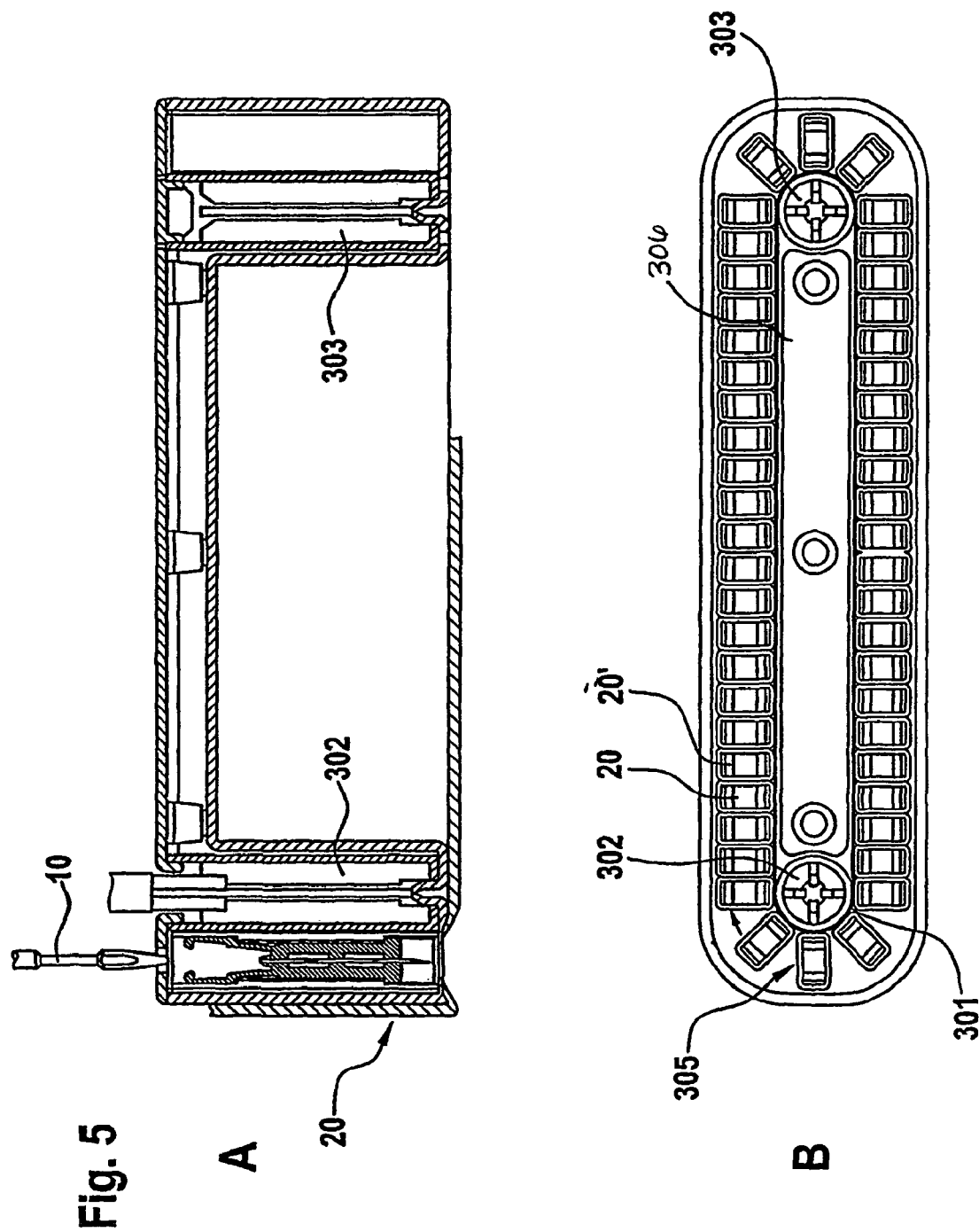
FIG. 5A is a side view of a magazine of lancing units.
FIG. 5B is a top view of a magazine of lancing units.

Referring to FIGS. 5A and 5B, an automated system containing lancing units 20 according to FIGS. 1A-1C is shown. The top view, FIG. 5B, shows how the lancing units 20, 20' etc., are attached next to one another on a belt 301. The belt 301 travels around two spaced apart rollers 302, 303. One of the rollers is driven by a motor (not shown) such that the lancing units 20, 20' are successively moved through a coupling position 305. As shown in FIG. 4A a form-fitting coupling of a driving plunger 10 to a lancing unit 20 located in the lancing position (305) is possible in this position.

Figure 6:
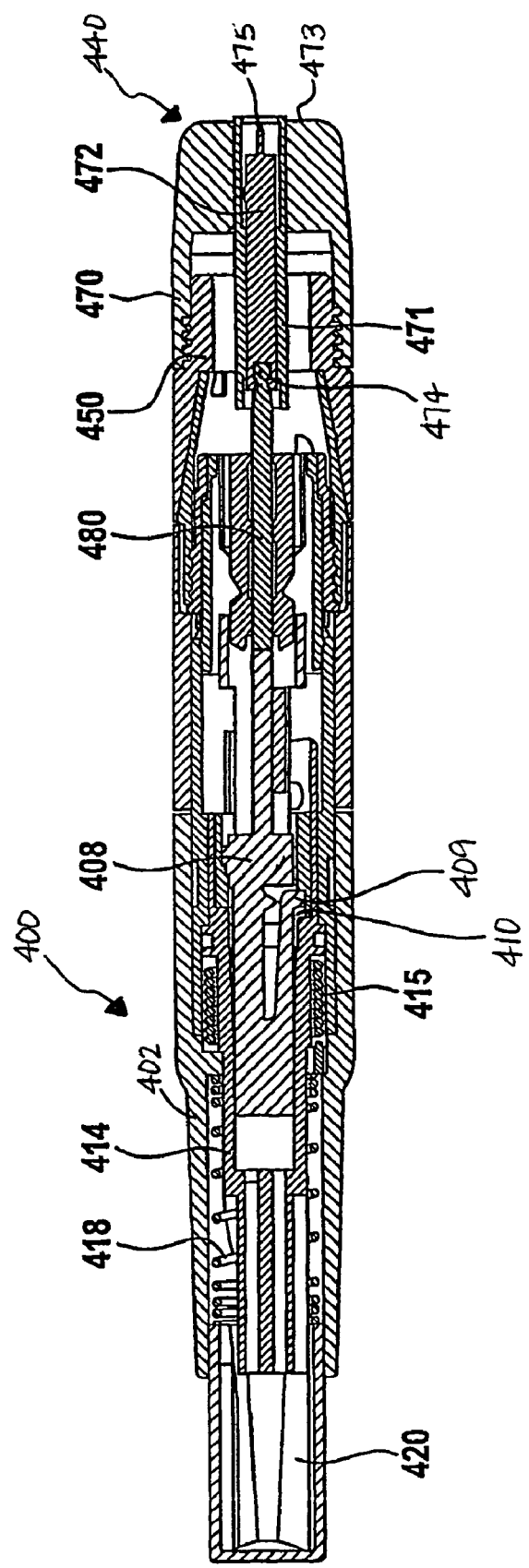
FIG. 6 is a cross-sectional view of a system consisting of a drive unit and lancing unit.

Referring now to FIG. 6, a drive unit 402 is coupled to a lancing unit 440 similar to the embodiment shown in FIGS. 1A-1C. The drive system 400 shown corresponds to the European Patent Application No. 0 010 2503.0. In drive system 400 a sleeve 414 is axially rotated by pressing a press button 420 against the tension of a spring 418 such that a second spring 415 is tensioned. The sleeve 414 is locked in an end position such that the second spring 415 remains tensioned. When the user releases the locking device, the spring 415 relaxes and the sleeve 414 is rotated in the opposite direction to that of the tensioning process. A groove 410 is located in the sleeve 414 which acts as a guide block for the propelling cylinder 408 which has a pin 409 or similar means which engage in the groove 410. Hence the rotation of the sleeve 414 is converted into a translation of the propelling cylinder 408. The propelling cylinder 408 transfers its forwards movement to the driving plunger 480 which has a holding area 432 at its front end.

The drive unit 402 has a holding area 450 onto which a lancing unit 440 can be mounted or screwed on. The lancing unit 440 comprises a cap 470 which has a surface 473 for pressing down on the skin surface. The cap 470 contains a sleeve 471 which has a lancet 472 that has holding devices 474 on the end facing away from the needle tip 475. The holding devices 474 of the lancet 472 correspond to the holding devices 32a, 32b of FIGS. 1A-1C. FIG. 5A also shows that a form-fitting connection of the lancet 472 and driving plunger 480 is accomplished by attaching the cap 470 to the driving device 402.

Figure 7:
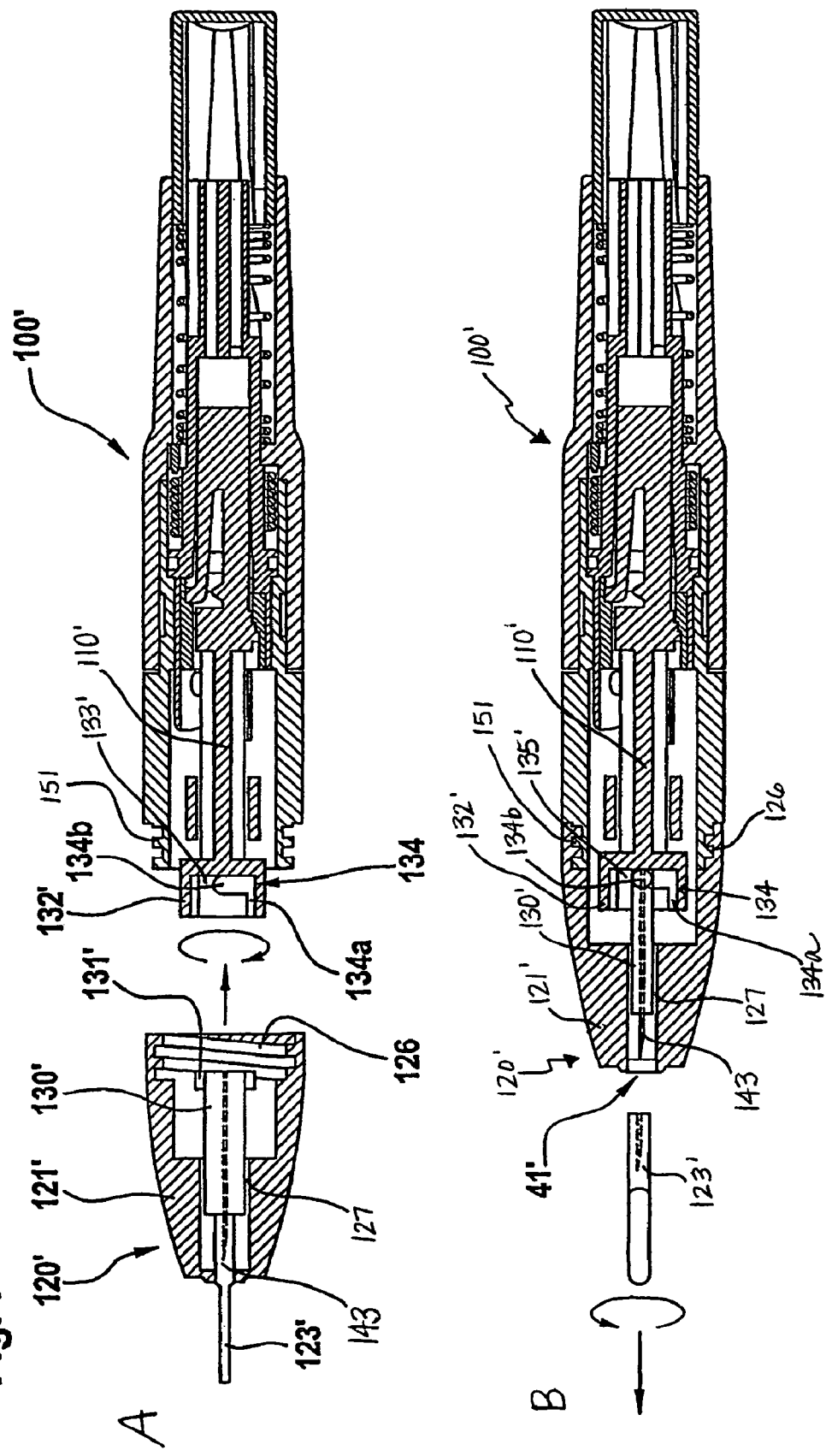
FIG. 7A is a cross-sectional view of a partially disassembled system having a dimensionally stable holding device.
FIG. 7B is a cross-sectional view of a system having a dimensionally stable holding device.

Referring now to FIGS. 7A and 7B, a system for withdrawing body fluids which has many similarities with the system shown in FIGS. 3A-3C is shown. Particular reference is made to the description of the drive and tensioning mechanism for FIGS. 3A-3C and FIG. 6. The system according to FIGS. 7A and 7B has a lancing unit 120' with a cap 121' and a lancet 130'. There is an axial passage 127 in the cap 121' through which the lancet 130' can pass during the lancing process. The passage 127 and lancet 130' preferably match one another in such a manner that the lancet 130' is guided axially during the lancing process with only a slight play in the transverse direction. The cap 121' has a thread 126 at its rear end which can be screwed onto a corresponding thread 151 of the drive unit 100'. The end of the lancet 130' opposite to the needle tip 143 has one or more (in the case shown two) pins 131' which make a form fit with the holding device 132' when the cap 120' is placed or screwed onto the drive unit 100'. For this purpose the holding device 132' has a recess 134 or groove that has an axial member 134a and a member 134b arranged at right angles thereto.

When the cap 120' is placed on the drive unit 100' the pins 131' come into the axial part of the groove 134 and move through this groove to the level of the transverse part of the groove. When the cap 120' is screwed onto the drive unit 100', the pins 131' move from the end of the axial part into the transverse part of the groove up to the opposite end 135'. As shown in FIG. 7B, the lancet 130' is held axially by the holding device 132' by means of the pins 131' such that a guided lancing movement can be carried out with the lancet 130'. Due to the position of the pins 131' in the transverse part of the grooves 134 the lancet 130' can be moved such that the needle tip 143 emerges and is also retracted. As shown in FIG. 7B the form-fitting connection between the lancet 130' and holding device 132' is achieved without wedging or locking. The coupling principle shown in FIGS. 7A and 7B of the lancet 130' and driving plunger 110' can also be accomplished in a converse manner, i.e. with a corresponding holding device of the lancet and a holding area on the plunger or drive.

Figure 8:
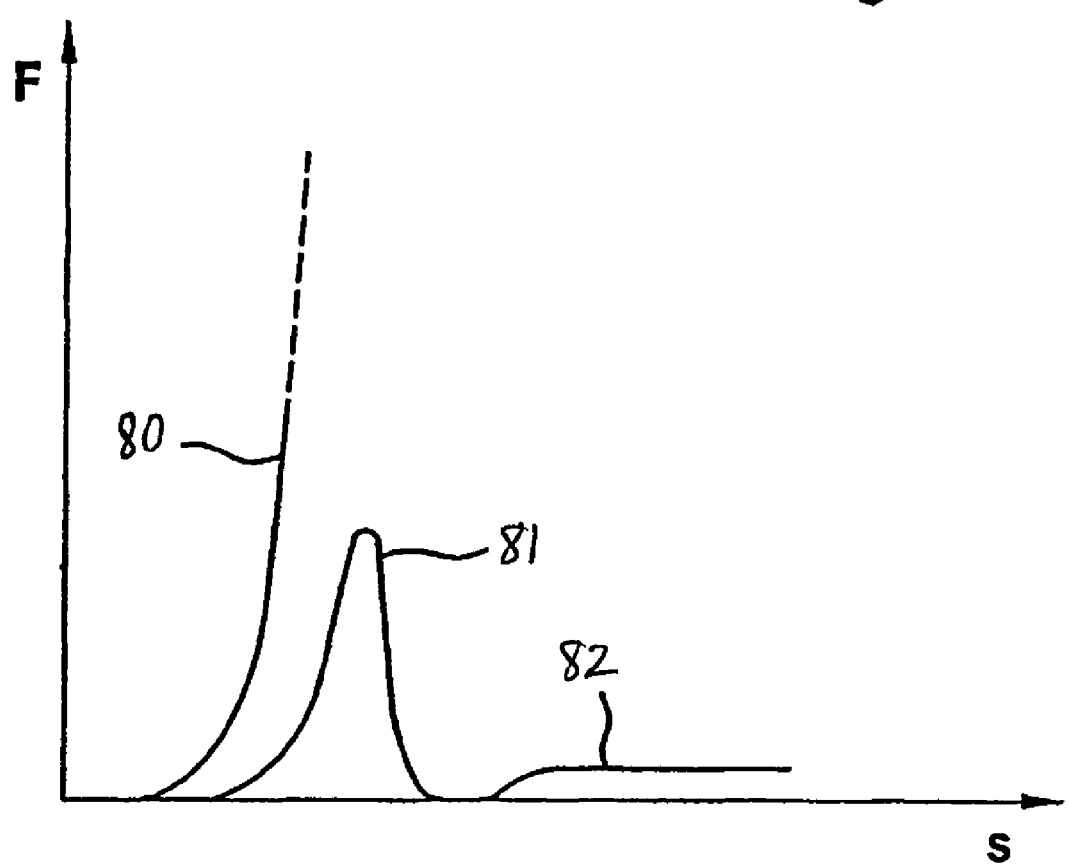
FIG. 8 is a force-path diagram for various types of coupling.

Referring now to FIG. 8, a graph containing force (F)—path (s) curves is shown schematically for the process of coupling the drive to the lancet for press-fitting (80), locking (81) and form-fitting (82). As demonstrated by curve 80, it can be seen that when using a press fit the force increases substantially until the lancet is released from the position in which it is held by a holding element or a spring. In the case of a locking device the force increases during the locking and decreases again after locking, as shown by curve 81. In the case of a form fit, shown by curve 82, only very small forces are necessary to move the holding elements together.

Referring now to FIGS. 9A-9C, a further development of the system of FIGS. 1A-1C is shown. The driving plunger 10' has a holding area 11' which has a circumferential slanted surface 12' on its upper side which fits between the slanted surfaces 33a', 33b' of the hooks 32a', 32b' during the lancing process. The end 13' of the driving plunger 10' rests on the end 29' of the needle 31'. Pressing together the flexible hooks 32a', 32b' causes the sloping surfaces 33a', 33b' on the inner side of the hooks 32a', 32b' to be pressed against sloping surfaces 12' on the upper side of the holding area 11' such that the holding area 11' is pressed onto the end 29' of the needle 31' thus forming a play-free connection of the holding area 11' and lancet 30' in the direction of lancing. This fit results in a very precise interlock between the lancet 30' and driving plunger 10' which compensates for (manufacturing) tolerances and thus eliminates play during the lancing and return movement.

The holding device in the form of hooks 32a', 32b' is also designed such that the free ends 38' of the hooks 32a', 32b' engage in recesses 42 in the sleeve 40'. This prevents the lancet 30' from accidentally slipping out of the sleeve 40'. As shown by the transition from FIG. 9A to FIG. 9B the free ends 38' of the hooks 32a', 32b' are initially positioned in the recesses 42 at the beginning of the lancing process. As the hooks 32a', 32b' are pressed together during insertion into the tapered sleeve 40' they enclose the holding area 11' of the driving plunger 10'.

Figure 9:
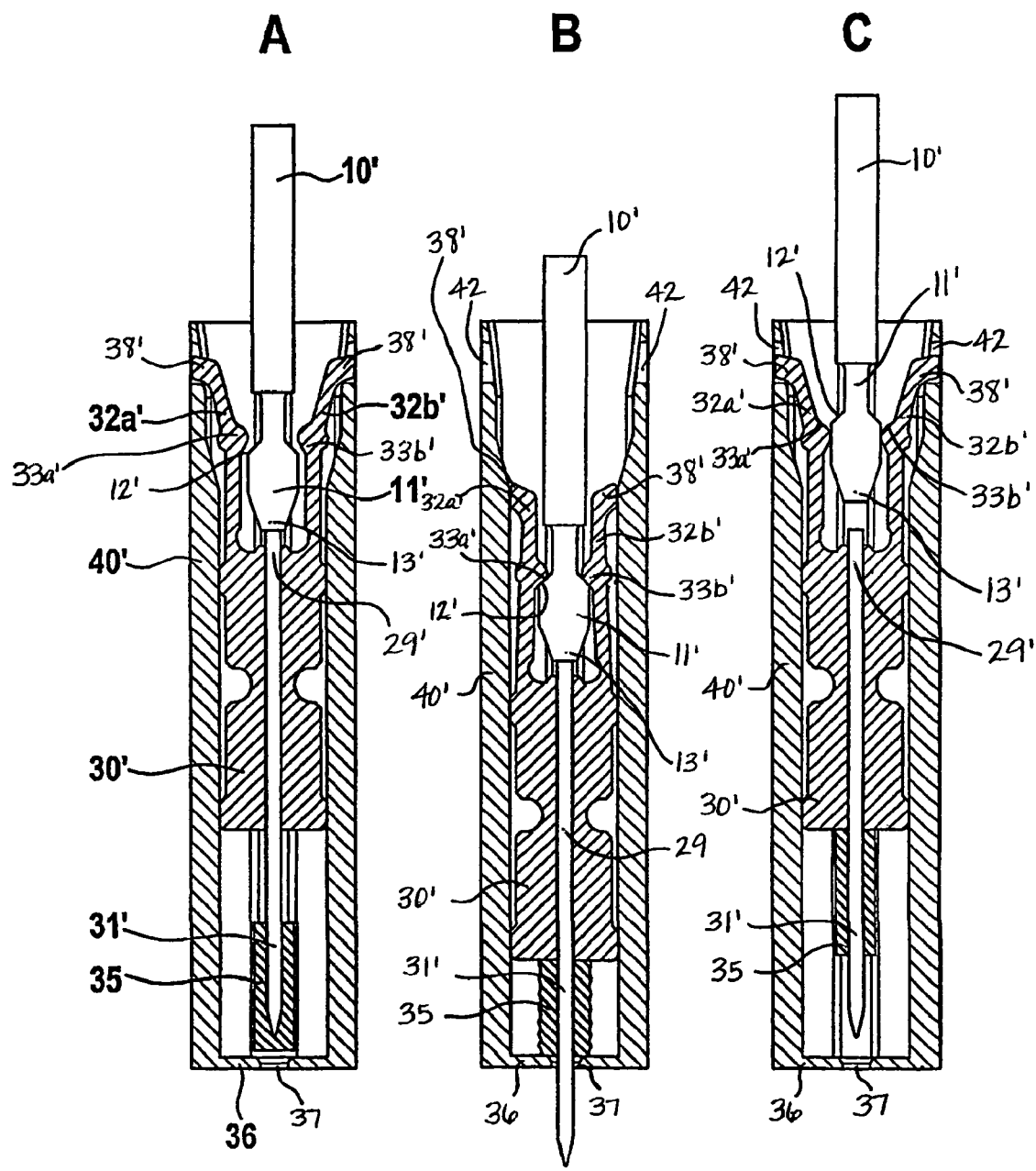
FIGS. 9A-9C are cross-sectional views of a lancing unit with a sterile protection, shown at three different positions (A,B,C).

FIG. 9 also shows that the needle tip is arranged in a material 35. This material 35 is preferably an elastomer which tightly encloses the needle tip to effectively prevent contamination of the needle tip. Suitable elastomers are styrene oligoblock copolymers, thermoplastic polyolefins, thermoplastic polyurethanes, thermoplastic copolyesters and thermoplastic copolyamides. The material 35 used to prevent contamination of the needle tip is further explained in PCT Published Application WO 01/66010, the disclosure of which is herein expressly incorporated by reference. In the initial position shown in FIG. 9A, before lancing the needle tip is located in the elastomer 35 which is pierced by the needle tip when a puncture is carried out as shown in FIG. 9B. For this purpose, the underside of the sleeve 40' has a plate 36 with a central opening 37. The plate 36 prevents the elastomer 35 from emerging through the opening 37 so that the elastomer 35 is pierced when the needle 31' passes through the central opening 37. When the lancet 30' is retracted, the elastomer 35 remains on the needle 31' and the needle tip is now exposed as shown in FIG. 9C.

Figure 10:
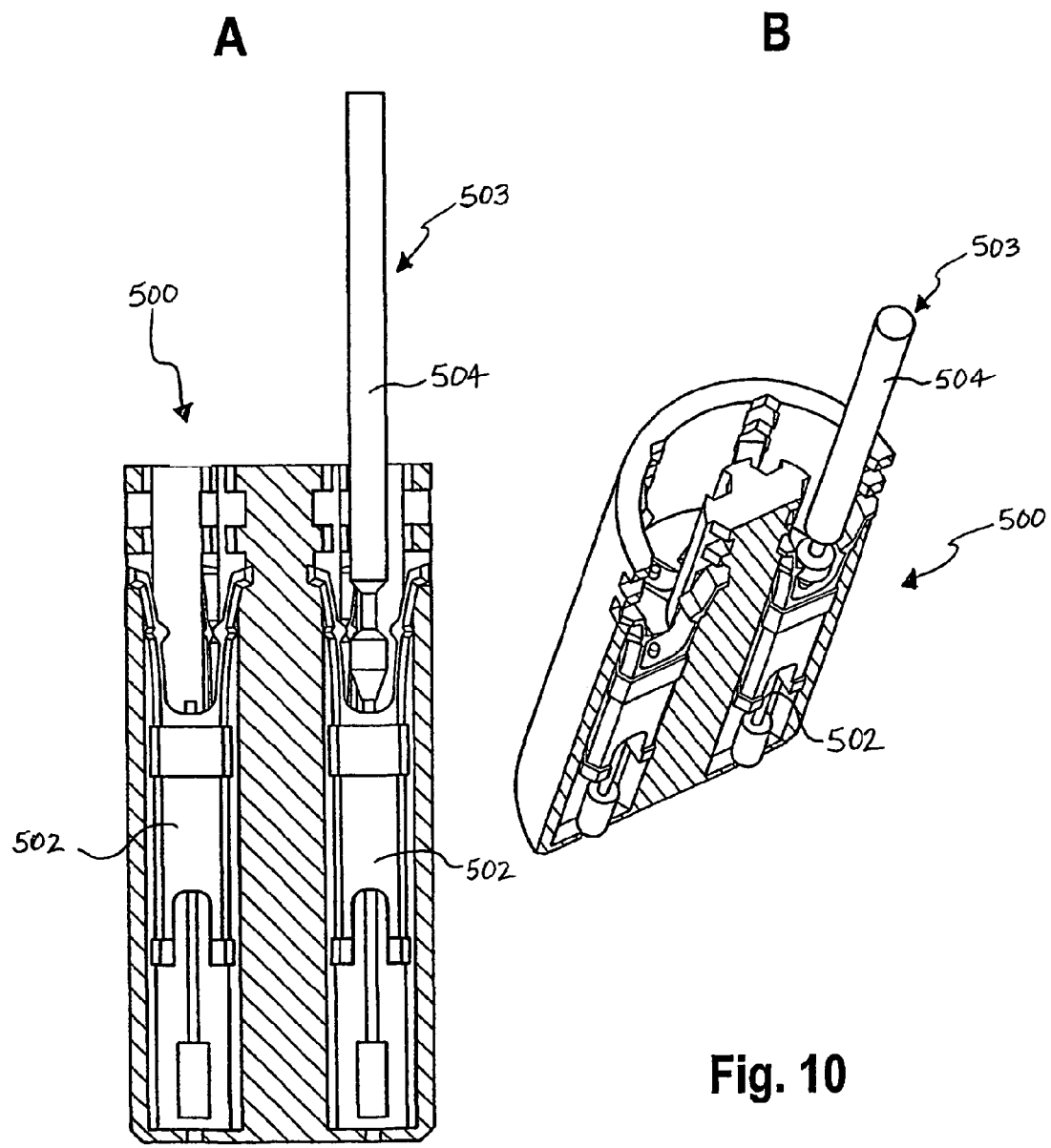
FIGS. 10A and 10B are cross-sectional views of a barrel-shaped magazine.

Referring now to FIGS. 10A and 10B, a cross-section (FIG. 10A) and a perspective view (FIG. 10B) of a cylindrical magazine 500 based on lancets according to FIGS. 1A-1C and 9A-9C are shown. Such a magazine 500 enables new lancets 502 to be coupled to the drive 503 in a simple manner. For this purpose the driving plunger 504 can, for example, be fixed relative to a lancet 502 and the barrel-shaped magazine 500 shown in FIG. 10 is rotated like a revolver barrel such that unused lancets 502 are moved into the position for coupling to the driving plunger 504.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

The invention claimed is:

1. Lancet comprising a needle and a needle tip wherein the needle tip is embedded in an elastomer before a puncture and wherein the elastomer is pierced by the needle during a puncture process in order to free the needle tip, wherein the lancet is used for withdrawal of blood, characterized in that the elastomer remains on the needle when the lancet is at a fully retracted position and the needle tip is exposed at the fully retracted position.

2. The lancet according to claim 1, characterized in that the elastomer tightly surrounds the needle tip.

3. The lancet according to claim 1, characterized in that the elastomer is selected from the group comprising styrene-oligoblock copolymers, thermoplastic polyolefins, thermoplastic polyurethanes, thermoplastic copolyesters and thermoplastic copolyamides.

4. The lancet according to claim 1, characterized in that it has a base body made of plastic in which a metal needle is located.

5. The lancet according to claim 1, characterized in that it has a holding device with holding elements to make a form-fitting connection with a plunger of a drive unit.

6. Lancing unit comprising at least one lancet according to claim 1 as well as a housing in which the at least one lancet is arranged in a resting position.

7. System for withdrawing blood, comprising:
a drive unit having a plunger which is moved from a resting position into a lancing position in order to carry out a lancing process and
a lancing unit according to claim 6 in which a lancet with a needle is located, where said lancet is arranged within the lancing unit in the resting position of the plunger and is displaced by the plunger when it moves into the lancing position in such a manner that the needle at least partially emerges through an exit opening in the lancing unit.

8. The system according to claim 7, characterized in that the plunger and lancet are coupled together by a form fit in order to carry out the lancing process.

9. The system according to claim 7, characterized in that the plunger has a holding area which is held in a form fitting manner on the lancet by a holding device.

10. The system according to claim 7, in which the lancing unit is detachably attached to the drive unit.

11. The system according to claim 7, which has a magazine containing a plurality of the lancets which can be successively coupled to the plunger of the drive unit.

12. The system according to claim 7, wherein:
the lancet includes at least one holding element configured to move transversely to a direction the plunger moves in order to carry out the lancing process; and
the plunger and the holding element are decoupled when at the resting position.

13. The system according to claim 12, further comprising:
a sleeve in which the lancet is disposed; and
wherein the holding element has a shoulder configured to retain the needle tip within the sleeve when the lancet is retracted and the needle tip is exposed.

14. The lancing unit according to claim 6, characterized in that the lancing unit contains a sleeve in which the lancet is movably located.

15. The lancing unit according to claim 14, characterized in that an underside of the sleeve has a plate with a central opening wherein the plate prevents the elastomer from emerging through the opening so that the said elastomer is pierced when the needle emerges through the central opening.

16. Method for temporarily extending a needle out of a device for withdrawing blood wherein the needle has a needle tip which is embedded in an elastomer before a puncture, comprising:
carrying out the puncture during which the elastomer is pierced by the needle and
retracting a lancet to a fully retracted position during which the elastomer remains on the needle and the needle tip is exposed in the fully retracted position.

17. The method according to claim 16, comprising:
coupling the lancet to a plunger of a drive unit in a form-fitting manner, wherein either the plunger has a holding area and the lancet has a holding, device or the lancet has a holding area and the plunger has a holding device,
moving the plunger from a resting position in which the needle of the lancet is arranged within a lancing unit into a position in which the needle emerges from an exit opening of the lancing unit, and
retracting the plunger in order to pull the needle back into the lancing unit.

18. Method for temporarily extending a needle from a device for withdrawing blood, comprising:
coupling a lancet to a plunger of a drive unit in a form-fitting manner where either the plunger has a holding area and the lancet has a holding device or the lancet has a holding area and the plunger has a holding device,
moving the plunger from a resting position in which the needle of the lancet is located inside a lancing unit into a position in which the needle emerges from an exit opening of the lancing unit, wherein at least one holding element of the holding device is moved transversely to a longitudinal direction by means of a longitudinal movement of the holding device during said moving the plunger from the resting position such that at least one holding element at least partially closes around the holding area, and
moving the plunger back in order to retract the needle into the lancing unit.

19. The method as claimed in claim 18, in which the lancet is coupled to the drive unit by attaching the lancing unit to the drive unit.

20. The method as claimed in claim 18, in which the lancet and plunger are disconnected by removing the lancing unit from the drive unit.

21. The method as claimed in claim 18, wherein:
the lancet has a needle with a needle tip which is located in an elastomer before a puncture;
said moving the plunger from the resting position includes carrying out the puncture during which the elastomer is pierced by the needle; and
said moving the plunger back includes retracting the lancet during which the elastomer remains on the needle and the needle tip is exposed.

22. The method as claimed in claim 21, further comprising:
wherein the holding device includes at least one holding element; and
coupling the holding element with the holding area by moving the holding element in a transverse direction during said moving the plunger from the resting position.

23. The method as claimed in claim 22, further comprising:
decoupling the holding element from the holding area after said moving the plunger back; and
retaining the needle tip in the lancing unit by engaging a shoulder of the holding element with the lancing unit.

* * * * *